Sept. 25, 1962 R. S. MOORE Plant Pat. 2,177
MINIATURE ROSE PLANT
Filed Aug. 21, 1961
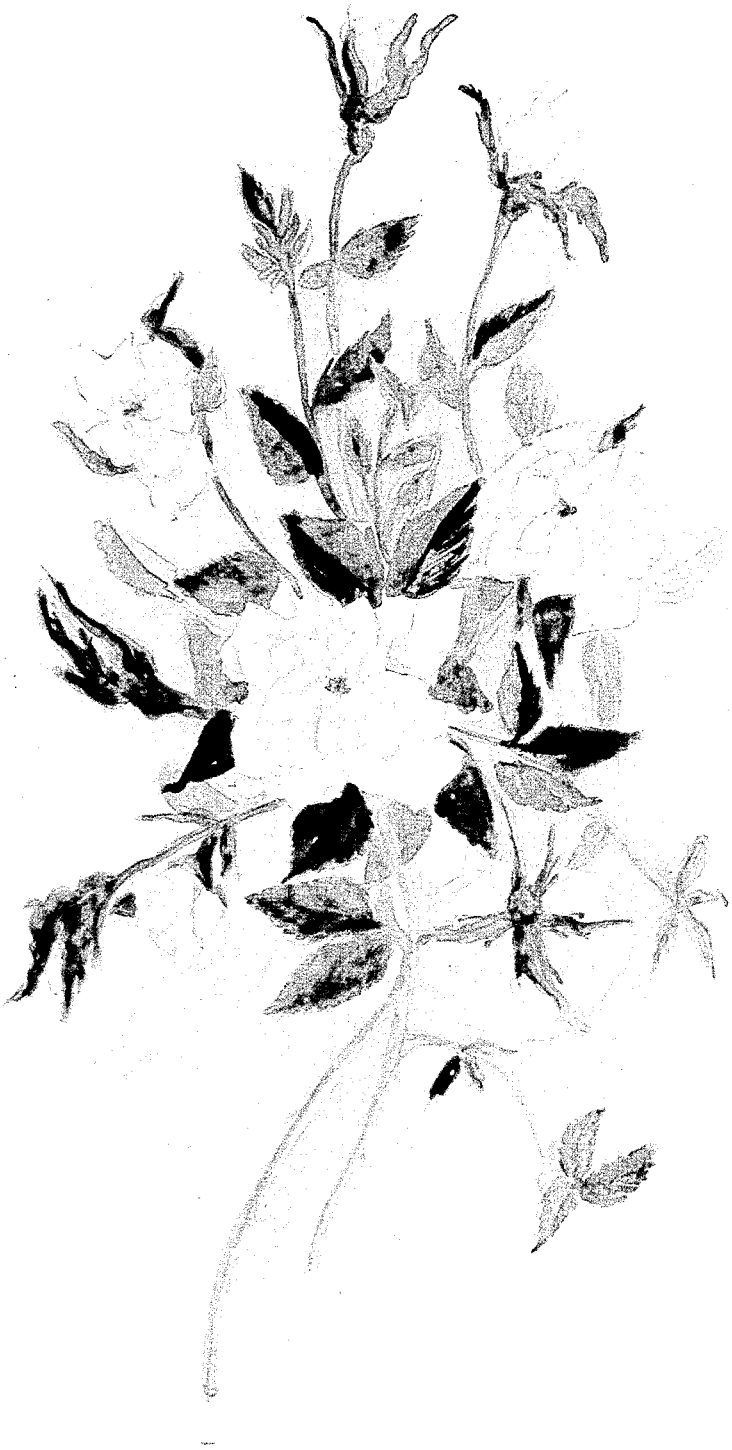
WITNESS
Jeanette Copley
INVENTOR
Ralph S. Moore
Webster & Webster
ATTYS.

United States Patent Office

Plant Pat. 2,177
Patented Sept. 25, 1962

2,177

MINIATURE ROSE PLANT

Ralph S. Moore, 2519 E. Mineral King, Visalia, Calif.

Filed Aug. 21, 1961, Ser. No. 132,995
1 Claim. (Cl. 47—61)

This invention relates to a new and distinct variety of miniature rose plant of hardy, compact, dwarf, bush, type.

The variety is particularly characterized by small, very double, flowers attractively styled like a large hybrid tea rose; the flowers when newly open being a soft green near the base of the petals and thence shading outward to a near white, and later becoming substantially an entire white or ivory white.

The variety is additionally characterized by a plant:

That roots easily from cuttings and transplants well.

That grows well in any type of soil, and is tolerant to iodine salts therein.

That has clean glossy green foliage, and is only moderately thorny.

That blooms freely even in hot weather, with the flowers having a firm substance to the petals.

That can be readily and effectively budded on understock stems to produce a very pleasing miniature tree rose.

In comparison to the miniature rose Jackie (unpatented), and to which in general it is similar, the present variety has a better growing habit and a distinctive flower color that is more dependable and consistent.

The variety was originated by me in my nursery located at Visalia, California, under conditions of careful control and observation, as a cross between Golden Glow (United States Plant Patent No. 263) as the seed parent, and Zee (unpatented) as the pollen parent; Zee being a miniature rose variety heretofore originated by me, used only for rose plant breeding, and which has not been introduced to the trade.

Subsequent to origination of the variety I successfully asexually reproduced it, in my nursery located as aforesaid, by budding as well as cuttings; the reproductions having run true in all respects.

The figure of the drawings illustrates a spray, including foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bush; seedling; greenhouse; garden decoration; potted plant.
Class: Hybrid miniature.

*Flowers*

Continuity: Continuous.
Fragrance: Moderate.
Flowers borne: Singly, several to stem. In irregular cluster on strong, medium length stems.
Quantity of bloom: Abundant, both outdoors and in greenhouse.

Bud:
*Peduncle.*—Medium length; heavy; erect; stiff; medium green; smooth.
*Before calyx breaks.*—Size—small. Form—pointed; with foliaceous appendages on the surface of the bud; with foliaceous parts extending beyond the tip of the bud equal to one-fourth of its length. Color—normal green.
*As calyx breaks.*—Greenish white.
*As first petal opens.*—Size—small. Form—pointed, ovoid. Color—both outside and inside near white, or pale greenish white.

Bloom:
*Size when fully open.*—Small, averaging 1½".
*Petalage.*—Very double, with from 60 to 70 petals arranged regularly.
*Form.*—Full, high center at first, becoming globular. Petals at first, and at maturity, loosely rolled outward.

Petals: Thick; leathery; satiny both outside and inside.
*Shape.*—Outside—obovate, tips acute. Intermediate —lanceolate. Inside—lanceolate.
*Color.*—Newly opened flower from plant grown outdoors (July 1961): Outside petal—both outside and inside surfaces—Uranium Green, 63/2 at base, shading to near white on the outer two-thirds of the petal. Intermediate petal—both ouside and inside surfaces—between Uranium Green, 63/2 and Dresden Yellow 64/2 at the base, shading to near white on the outer two-thirds of the petal. Inner petal—both outside and inside surfaces—Dresden Yellow, 64/2. A flower that was open for three days outdoors (July 1961)—all petals, both outside and inside surfaces, substantially white or near white.
*Behavior.*—Persist for a time, then drop. Affected by cold weather to the extent that petals sometimes not so well formed.
*Flower longevity (June).*—Bush in garden—four to five days. Cut flowers kept at living room temperature—three days.

*Reproductive Organs*

Stamens: Very few to none; mixed with petaloids.
Filaments: White; few or none; without anthers.
Pollen: None.
Pistils: Few.
Styles: Uneven.
Stigma: Green or brownish, usually malformed.
Ovaries: All enclosed in calyx.
Hips: None.
Sepals: Permanent, peduncle separates and falls after a time. Color—green.
Seeds: None.

*Plant*

Foliage:
*Leaves.*—Compound of five leaflets; abundant; small; leathery; glossy.
*Leaflets.*—Shape—lanceolate. Apex—acute. Margin—serrate. Color: Mature—upper surface — normal green; under surface — normal green. Young—upper surface—normal green; under surface—grey green with red tinting. Rachis—medium strength; upper side grooved; under side sparsely thorny, usually with three small thorns. Stipules—medium length; narrow width, with medium length points turning out at an angle of less than 45 degrees.

Growth:
*Habit.*—Dwarf; bushy; much branched.
*Growth.*—Vigorous.
*Canes.*—Medium to heavy.
*Main stems.* — Color — green. Thorns — several; hooked downward, with short round base. Prickles—none. Hairs—none.
*Branches.*—Color—green. Thorns—few to several; short; hooked downward, with short round base. Prickles—none. Hairs—none.
*New shoots.*—Color—green, with some bronze at times. Thorns—few; hooked downward, with short round base. Prickles—none. Hairs—none.

The miniature rose plant and its flowers as herein described may vary in slight detail due to climatic and soil conditions under which the variety may be grown; the present description being of the variety as grown at Visalia, California.

The following is claimed:

A new and distinct variety of miniature rose plant of hardy, compact, dwarf, bush type, as illustrated and described, characterized by small, very double flowers styled like a large hybrid tea rose, the flowers when open being a soft green near the base of the petals and thence shading outward to a near white and later becoming substantially an entire white or ivory white; and further characterized in comparison to the Jackie rose and which in general it most nearly resembles, by a better growing habit and the distinctive flower color which is more dependable and consistent.

No references cited.